United States Patent [19]

Fabry et al.

[11] Patent Number: 5,691,300
[45] Date of Patent: Nov. 25, 1997

[54] RINSE AIDS FOR THE MACHINE WASHING OF HARD SURFACES

[75] Inventors: Bernd Fabry, Korschenbroich; Juergen Haerer, Duesseldorf; Birgit Burg, Alpen; Marica Nejtek, Monheim; Peter Jeschke, Neuss; Udo Hees, Mayen, all of Germany

[73] Assignee: Henkel Kommanditgesellschaft auf Aktien, Duesseldorf, Germany

[21] Appl. No.: 569,238

[22] PCT Filed: Jul. 4, 1994

[86] PCT No.: PCT/EP94/02187

§ 371 Date: Feb. 28, 1996

§ 102(e) Date: Feb. 28, 1996

[87] PCT Pub. No.: WO95/02666

PCT Pub. Date: Jan. 26, 1995

[30] Foreign Application Priority Data

Jul. 12, 1993 [DE] Germany .................. 43 23 253.1

[51] Int. Cl.⁶ .................. C11D 3/32; C11D 1/825; C11D 1/72; C11D 3/22
[52] U.S. Cl. .................. 510/514; 510/502; 510/221; 510/223; 510/423; 510/433; 510/434; 510/470; 510/475; 510/477; 510/506
[58] Field of Search .................. 510/514, 502, 510/221, 223, 423, 433, 434, 470, 475, 477, 506

[56] References Cited

U.S. PATENT DOCUMENTS

| | | | |
|---|---|---|---|
| 1,985,424 | 12/1934 | Piggott | 260/124 |
| 2,016,962 | 10/1935 | Flint et al. | 260/127 |
| 2,703,798 | 3/1955 | Schwartz | 260/211 |
| 4,443,363 | 4/1984 | Klinger et al. | 252/547 |
| 5,009,814 | 4/1991 | Kelkenberg et al. | 252/548 |
| 5,376,310 | 12/1994 | Cripe et al. | 252/548 |
| 5,545,354 | 8/1996 | Ofosu-Asante | 510/237 |

FOREIGN PATENT DOCUMENTS

| | | |
|---|---|---|
| 0054895 | 6/1982 | European Pat. Off. . |
| 0095136 | 11/1983 | European Pat. Off. . |
| 0285768 | 10/1988 | European Pat. Off. . |
| 0301298 | 2/1989 | European Pat. Off. . |
| 0432836 | 6/1991 | European Pat. Off. . |
| 1580491 | 9/1969 | France . |
| 1261861 | 2/1968 | Germany . |
| 2200040 | 8/1973 | Germany . |
| 2226870 | 12/1973 | Germany . |
| WO8809369 | 12/1988 | WIPO . |
| WO 903977 | 4/1990 | WIPO . |
| 92/06156 | 4/1992 | WIPO . |
| 92/06158 | 4/1992 | WIPO . |
| 92/06160 | 4/1992 | WIPO . |
| 92/06161 | 4/1992 | WIPO . |
| WO 926152 | 4/1992 | WIPO . |
| WO 926153 | 4/1992 | WIPO . |
| WO 926154 | 4/1992 | WIPO . |
| WO 926155 | 4/1992 | WIPO . |
| WO 926157 | 4/1992 | WIPO . |
| WO 926159 | 4/1992 | WIPO . |
| WO 926162 | 4/1992 | WIPO . |
| WO 926164 | 4/1992 | WIPO . |
| WO 926170 | 4/1992 | WIPO . |
| WO 926171 | 4/1992 | WIPO . |
| WO 926172 | 4/1992 | WIPO . |
| WO9206984 | 4/1992 | WIPO . |
| WO9222629 | 12/1992 | WIPO . |

*Primary Examiner*—Paul Lieberman
*Assistant Examiner*—Charles I. Boyer
*Attorney, Agent, or Firm*—Ernest G. Szoke; Wayne C. Jaeschke; Real J. Grandmaison

[57] ABSTRACT

A process for rinsing hard surfaces comprising contacting the hard surfaces with an aqueous rinse aid composition containing fatty acid-N-alkyl polyhydroxyalkyl amides corresponding to formula I:

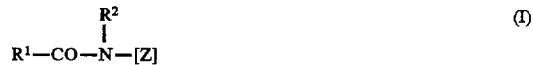

wherein $R^1CO$ is an aliphatic acyl radical containing 6 to 22 carbon atoms, $R^2$ is hydrogen, an alkyl or hydroxyalkyl radical containing 1 to 4 carbon atoms, and [Z] is a linear or branched polyhydroxyalkyl radical containing 3 to 10 carbon atoms and 3 to 10 hydroxyl groups.

13 Claims, No Drawings

RINSE AIDS FOR THE MACHINE WASHING OF HARD SURFACES

BACKGROUND OF THE INVENTION

1. Field of the Invention

This invention relates to new rinse aids essentially containing fatty acid N-alkyl polyhydroxyalkyl glucamides for the machine washing of hard surfaces and to the use of these substances for the production of the rinse aids.

2. Discussion of Related Art

Commercial rinse aids are mixtures of low-foaming fatty alcohol polyethylene/polypropylene glycol ethers, solubilizers (for example cumene sulfonate), organic acids (for example citric acid) and solvents (for example ethanol). The function of rinse aids is to influence the interfacial tension of the water in such a way that it is able to drain from the rinsed surfaces in the form of a thin coherent film, so that no water droplets, streaks or films remain behind during the subsequent drying process. A review of the composition of rinse aids and methods for testing their performance can be found in W. Schirmer et al. in Tens. Surf. Det. 28, 313 (1991).

In addition, where modern phosphate-free low-alkali detergents are used for machine dishwashing, lime and silicate coatings can form on the rinsed surfaces and on the inside of the dishwashing machine because the calcium binding power of these detergents is lower than that of conventional phosphate-containing products. Troublesome lime and silicate coatings occur in particular when the rinsing water of the dishwashing machine has not been softened sufficiently, if at all, and a water hardness of 4° d is exceeded. In cases such as these, lime and silicate coatings can be effectively avoided by introducing citric acid into the final rinse cycle through the rinse aid. However, since the quantities of rinse aid normally added during the final rinse are very small (3 ml to 6 ml), the citric acid content in rinse said formulations intended to guarantee effective inhibition of coatings has to be relatively high to achieve an adequate acid or complexing capacity. Citric acid contents as high as these support the effect of the phosphate substitutes and guarantee spotless dishes.

International patent application WO 88/09369 describes water-based liquids for dishwashing machines which contain $C_{8-16}$ alkyl oligoglucosides, low-foaming fatty alcohol polyglycol ethers and alkali metal citrates. However, these liquids are unsuitable as rinse aids.

European patent application EP-A2 0 432 836 (Unilever) describes rinse aid formulations for dishwashing machines which contain only one surfactant, namely alkyl oligoglucosides, and foam inhibitors and thickeners as additional constituents. Foam inhibitors are an essential constituent of these formulations because alkyl oligoglucosides are generally high foamers and would cause unacceptable foaming in the described rinse aid formulations when used in dishwashing machines. However, defoamers are only effective providing they do not dissolve in the medium to be foam-inhibited. Accordingly, the alkyl oligoglucoside solutions and the foam inhibitors are not miscible with one another in the examples of rinse aids mentioned in this document. Accordingly, two phases would exist if a thickener providing for a certain degree of homogenization had not been used to disperse them. However, one disadvantage of such a formulation is the latent inhomogeneity caused by the foam inhibitor. The foam inhibitor and surfactant solution of the rinse aid separate after only a short time, despite the presence of a thickener. A product such as this is understandably unsuitable both for consumers of branded goods and for large-scale use, because both sectors require products which must remain stable in storage for prolonged periods, but at least for one year. Accordingly, the only suitable formulations are one-phase formulations in which all the constituents are homogeneously dissolved and which not only remain stable in storage, but also do not separate during the heating and cooling phase of the rinse cycle, i.e. phase stability must be guaranteed in the temperature range of the dishwashing machine of 0° C. to 65° C. On the other hand, the known products are so viscous as long as they remain homogeneous that they cannot be poured in through the rinse aid dispenser of a domestic dishwashing machine.

Various materials (glass, metal, silver, plastic, china) are washed in dishwashing machines. These various materials have to be thoroughly wetted in the final rinse cycle. Rinse aids containing alkyl polyglycosides as their only surfactant component satisfy these requirements to only a limited extent, if at all, so that the clear-rinse or drying effect is unsatisfactory, particularly on plastic surfaces.

In addition, only those ingredients which are completely biodegradable and toxicologically safe may now be considered for use in detergents, including rinse aid formulations. Particular interest is attached in this regard to solvent-free products.

Accordingly, the problem addressed by the present invention was to provide new ecologically and toxicologically safe formulations which, in regard to their performance properties, would give the same results as commercial rinse aids without having any of their disadvantages.

DESCRIPTION OF THE INVENTION

The present invention relates to rinse aids for the machine washing of hard surfaces containing fatty acid-N-alkyl polyhydroxyalkyl amides corresponding to formula (I):

in which $R^1CO$ is an aliphatic acyl radical containing 6 to 22 carbon atoms, $R^2$ is hydrogen, an alkyl or hydroxyalkyl radical containing 1 to 4 carbon atoms and [Z] is a linear or branched polyhydroxyalkyl radical containing 3 to 10 carbon atoms and 3 to 10 hydroxyl groups, and optionally other nonionic surfactants and typical auxiliaries and additives.

It has surprisingly been found that rinse aids containing fatty acid N-alkyl polyhydroxyalkyl amides and, in particular, fatty acid N-methyl glucamides not only show high ecotoxicological compatibility, they also satisfy the requirements which a branded product is expected to meet in regard to its performance properties.

Another advantage of the rinse aids according to the invention is that the preparation of homogeneous, low-viscosity and hence readily dispensable solutions does not require the use of any other, generally inert solubilizers which make no contribution to the drying or clear-rinse effect, such as for example sodium cumene sulfonate, ethanol or glucose syrup, except in cases where they are needed in small quantities for the incorporation of dyes and/or fragrances.

Finally, binary and ternary combinations of the fatty acid N-alkyl polyhydroxyalkyl amides with fatty alcohol polyglycol ethers, mixed ethers and/or alkyl oligoglucosides have proved to be particularly advantageous. Formulations such as these are extremely low-foaming and wet even different materials equally thoroughly. A particular clear-rinse effect is obtained on plastic surfaces.

Fatty Acid N-alkyl Polyhydroxyalkyl Amides

The fatty acid N-alkyl polyhydroxyalkyl amides are known substances which may normally be obtained by reductive amination of a reducing sugar with ammonia, an alkyl amine or an alkanolamine and subsequent acylation with a fatty acid, a fatty acid alkyl ester or a fatty acid chloride. A relevant synopsis can be found in H. Kelkenberg, Tens. Surf. Det, 25, 8 (1988). Processes for their production are described in U.S. Pat. Nos. 1,985,424, 2,016,962 and 2,703,798, in DE-AS 12 61 861 and in WO 92/06984.

The use of the fatty acid amides mentioned is also the subject of a number of publications. For example, EP-A10 285 768 (Hüls) describes their use as thickeners. FR-A 1 580 491 (Henkel) describes water-based detergent mixtures based on sulfates and/or sulfonates, nonionic surfactants and optionally soaps which contain fatty acid N-alkyl glucamides as foam regulators.

International patent applications WO 92/6153; 6156; 6157; 6158; 6159 and 6160 (Procter & Gamble) describe mixtures of fatty acid N-alkyl glucamides with anionic surfactants, sulfate and/or sulfonate surfactants, ether carboxylic acids, ether sulfates, methyl ester sulfonates and nonionic surfactants. The use of these substances in various laundry detergents, dishwashing detergents and cleaning products is described in WO 92/6152; 6154; 6155; 6161; 6162; 6164; 6170; 6171 and 6172 (Procter & Gamble). However, there is no reference in any of these documents to the advantageous use of these substances in rinse aid formulations.

The fatty acid amides to be used in the rinse aid formulations according to the invention are preferably derived from reducing sugars containing 5 or 6 carbon atoms, more particularly from glucose. Accordingly, the preferred fatty acid N-alkyl polyhydroxyalkyl amides are fatty acid N-alkyl glucamides corresponding to formula (II):

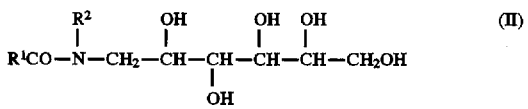

Fatty acid N-alkyl polyhydroxyalkyl amides corresponding to formula (I), in which $R^1CO$ is a $C_{6-12}$ acyl radical, $R^2$ is a methyl group and is a reduced glucose unit, are preferably used as raw materials for the production of the rinse aids according to the invention. Accordingly, fatty acid N-methyl glucamides obtained by reductive amination of glucose with methyl amine and subsequent acylation with a $C_{6-12}$ fatty acid or a corresponding derivative are particularly preferred. So far as the choice of the fatty acid is concerned, a $C_{8-10}$ fraction of the type formed, for example, as head fraction in the distillation of technical coconut oil fatty acid is particularly suitable.

Nonionic surfactants

Although nonionic surfactants are an optional component of the rinse aids according to the invention, they are nevertheless a preferred component. Basically, any nonionic surfactants may be used for this purpose although fatty alcohol polyethylene glycol ether, fatty alcohol polyethylene/polypropylene glycol ether, mixed ethers and/or alkyl oligoglucosides are particularly suitable.

Fatty alcohol polyethylene glycol ethers suitable for the purposes of the invention correspond to formula (III):

$$R^3O\text{-}(CH_2CH_2O)_{n1}H \qquad (III)$$

in which $R^3$ is a linear or branched $C_{6-22}$ and preferably $C_{12-18}$ alkyl and/or alkenyl radical and n1 is a number of 1 to 5.

The substances mentioned are known commercial products. Typical examples are adducts of, on average, 2 or 4 mol ethylene oxide with technical $C_{12/14}$ coconut oil fatty alcohol (Dehydol® LS-2 or LS-4, products of Henkel KGaA) or adducts of, on average, 4 mol ethylene oxide with $C_{14/15}$ oxoalcohols (Dobanol® 45-4, a product of Shell). The products may have a conventional or even a narrow-range homolog distribution.

Fatty alcohol polyethylene/polypropylene glycol ethers are understood to be nonionic surfactants corresponding to formula (IV)

$$R^4O\text{-}(CH_2CH_2O)_{n2}(CH_2CHO)_{m2}H \qquad (IV)$$
$$\qquad\qquad\qquad\qquad\qquad\quad |$$
$$\qquad\qquad\qquad\qquad\qquad CH_3$$

in which $R^4$ is a linear or branched $C_{6-22}$ and preferably $C_{12-18}$ alkyl and/or alkenyl radical, n2 is a number of 1 to 5 and m2 is a number of 1 to 4.

These substances are also known commercial products. A typical example is an adduct of, on average, 5 mol ethylene oxide and 4 mol propylene oxide with technical $C_{12/14}$ coconut oil fatty alcohol (Dehydol® LS-54, a product of Henkel KGaA).

Mixed ethers are end-capped fatty alcohol polyglycol ethers corresponding to formula (IV):

$$R^5O\text{-}(CH_2CH_2O)_{n3}(CH_2CHO)_{m3}R^6 \qquad (V)$$
$$\qquad\qquad\qquad\qquad\qquad\quad |$$
$$\qquad\qquad\qquad\qquad\qquad CH_3$$

in which $R^5$ is a linear or branched $C_{5-22}$ and preferably $C_{12-18}$ alkyl and/or alkenyl radical, n3 is a number of 1 to 10, m2 is 0 or a number of 1 to 4 and $R^6$ is a $C_{1-4}$ alkyl radical or a benzyl radical.

Typical examples are mixed ethers corresponding to formula (V), in which $R^5$ is a technical $C_{12/14}$ cocoalkyl radical, n3 is the number 5 or 10, m3 is 0 and $R^6$ is a butyl group (Dehypon® LS-54 or LS-104, products of Henkel KGaA). The use of butyl- or benzyl-terminated mixed ethers is particularly preferred for applicational reasons.

Alkyl oligoglucosides corresponding to formula (VI):

$$R^7O\text{-}[G]_p \qquad (VI)$$

in which $R^7$ is a $C_{5-12}$ alkyl radical, G is a glucose unit and p is a number of 1 to 10, are known substances which may be obtained by the relevant methods of preparative organic chemistry. Al 0 301 298 and WO 90/3977 are cited as representative of the extensive literature available on this subject.

The alkyl radical $R^7$ may be derived from primary alcohols containing 6 to 12 and preferably 8 to 10 carbon atoms. Typical examples are caproic alcohol, caprylic alcohol, capric alcohol, undecyl alcohol and lauryl alcohol and the technical mixtures thereof which are obtained, for example, in the hydrogenation of technical fatty acid methyl esters or during the hydrogenation of aldehydes from Roelen's oxo synthesis. $C_{8-10}$ alkyl oligoglucosides (DP=1 to 3), which are obtained as first runnings in the separation of technical $C_{8-18}$ coconut oil fatty alcohol by distillation and which may contain less than 6% by weight $C_{12}$ alcohol as an impurity, and alkyl oligoglucosides based on technical oxoalcohols (DP=1 to 3) are preferred.

The index p in general formula (VI) indicates the degree of oligomerization (DP degree), i.e. the distribution of mono- and oligoglucosides, and is a number of 1 to 10. Whereas p in a given compound must always be an integer and, above all, may assume a value of 1 to 6, the value p for a certain alkyl oligoglucoside is an analytically determined calculated quantity which is generally a broken number. Alkyl oligoglucosides having an average degree of oligomerization p of 1.1 to 3.0 are preferably used. Alkyl oligoglucosides having a degree of oligomerization below 1.7 and, more particularly, between 1.2 and 1.4 are preferred from the applicational point of view.

Auxiliaries and Additives

The most important additives are monobasic and polybasic carboxylic acids, preferably hydroxycarboxylic acids. Typical examples are maleic acid (monohydroxysuccinic acid), tartaric acid (dihydroxysuccinic acid); saturated aliphatic dicarboxylic acids, such as oxalic acid, malonic acid, succinic acid, glutaric acid, adipic acid; gluconic acid (hexane-1-pentahydroxycarboxylic acid), although anhydrous citric acid is preferred. They may be used in quantities of from about 1 to 50% by weight and are preferably used in quantities of from about 1 to 30% by weight.

Suitable other additives are, above all, dyes and fragrances.

Rinse Aid Formulations

Typical formulations of the rinse aids according to the invention may have the following composition for example (ad 100% by weight water):

0.5 to 20% by weight fatty acid N-alkyl polyhydroxyalkyl amides, 0 to 20% by weight alkyl oligoglucosides, 0 to 20% by weight fatty alcohol polyglycol ethers, 0 to 20% by weight mixed ethers, 1 to 50% by weight carboxylic acid.

Formulations Containing 1 to 10% by weight fatty acid N-alkyl glucamides, 3 to 10% by weight alkyl oligoglucosides, 3 to 10% by weight fatty alcohol polyglycol ethers and/or mixed ethers, 1 to 30% by weight citric acid are particularly advantageous.

Industrial Applications

The rinse aids according to the invention contain ecotoxicologically particularly safe ingredients, can be formulated without solvents and have an excellent wetting effect on various materials.

Accordingly, the present invention relates to the use of fatty acid N-alkyl polyhydroxyalkyl amides, more particularly fatty acid N-alkyl glucamides, for the production of rinse aids for the machine washing of hard surfaces, particularly dishes, in which they may be present in quantities of 0.5 to 20% by weight and preferably 1 to 10% by weight, based on the rinse aid as a whole.

The following Examples are intended to illustrate the invention without limiting it in any way.

EXAMPLES

I. Surfactants Used

A1) Octanoic acid N-methyl glucamide

A2) Decanoic acid N-methyl glucamide

A3) $C_{6-12}$ fatty acid N-methyl glucamide

B1) $C_{8-10}$ alkyl oligoglucoside (DP=1.6) Plantaren® APG 225, a product of Henkel KGaA, Düsseldorf, FRG C1) $C_{12/14}$ coconut oil fatty alcohol 4EO adduct Dehydol® LS-4, a product of Henkel KGaA, Düsseldorf, FRG C2) $C_{12/14}$ coconut oil fatty alcohol 5EO 4PO adduct Dehydol® LS-54, a product of Henkel KGaA, Düsseldorf, FRG C3) $C_{12/14}$ coconut oil fatty alcohol 10EO butyl ether Dehypon° LS-104, a product of Henkel KGaA, Düsseldorf, FRG.

II. Performance testing of the rinse aids a) Foaming Behavior:

The foam generation of the rinse aid was determined by means of a circulation pressure gauge. The rinse aid (3 ml) was introduced by hand into the final rinse cycle at 50° C. Foaming was evaluated on the following scale:

0 Points=no foaming

1 Point=slight foaming

2 Points=average foaming (still acceptable)

3 Points=heavy foaming b) Drying:

15 Minutes after the end of the rinse program, the door of the dishwashing machine was fully opened. After 5 minutes, drying was determined by counting the number of droplets remaining on the articles of crockery mentioned below. Evaluation was based on the following scale:

0 Points=more than 5 drops

1 Point=5 drops

2 Points=4 drops

3 Points=3 drops

4 Points=2 drops

5 Points=1 drop

6 Points=0 drops (optimal drying)

c) Clear-rinse effect:

After drying had been evaluated, the articles of crockery were removed from the dishwashing machine, left to cool for 30 minutes and then visually evaluated under illumination in a black box. The residual drops, streaks, coatings, cloudy films etc. remaining on the crockery and cutlery were evaluated. Evaluation:

0 Points=poor clear-rinse effect

8 Points=optimal clear-rinse effect d) Performance tests b) and c) were carried out in a Bauknecht GSF 1162 dishwashing machine using softened water (normal 65° C. program). 40 ml Somat® detergent (Henkel KGaA) were introduced during the wash cycle. The quantity of rinse aid used was 3 ml and was introduced by hand in the final rinse cycle at 50° C. The water had a salt content of 600 to 700 mg/l. Three rinse cycles were carried out for each rinse aid formulation. The following articles of crockery and cutlery were used to evaluate drying and the clear-rinse effect:

○ 6 "Neckar-Becher" glasses (Schott-Zwiesel)

○ 3 "Brasilia" stainless steel knives (WMF)

○ 3 white china plates (Arzberg)

○ 3 red plastic plates (Haßmann "Valon-Eßteller")

EXAMPLES 1 to 3:

TABLE 1

Rinse aids containing fatty acid N-methyl glucamides
Percentages as % by weight
ad 10% by weight water

| Ex. | A | c(A) % | CA % | FR % | St. °C. | App. | F |
|---|---|---|---|---|---|---|---|
| 1 | A1 | 15.0 | 3.0 | 0.5 | >70 | Clear | 0 |
| 2 | A2 | 15.0 | 3.0 | 0.5 | >70 | Clear | 0 |
| 3 | A3 | 15.0 | 3.0 | 0.5 | >70 | Clear | 1 |

Legend:
c(A): Concentration of A
CA: Citric acid, anhydrous
FR: Fragrance
St.: Stability
App.: Appearance of the solution
F: Foaming

EXAMPLES 4 to 6:

TABLE 2

Rinse aids containing fatty acid N-methyl glucamides and
fatty alcohol polyethylene glycol ethers
Percentages as % by weight
ad 100% by weight water

| Ex. | Glu | c(Glu) % | c(C1) % | CA % | FR % | St. °C. | App. | F |
|---|---|---|---|---|---|---|---|---|
| 4 | A1 | 9.0 | 6.0 | 3.0 | 0.5 | >70 | Clear | 0 |
| 5 | A2 | 9.0 | 6.0 | 3.0 | 0.5 | >70 | Clear | 1 |
| 6 | A3 | 9.0 | 6.0 | 3.0 | 0.5 | >70 | Clear | 1 |

EXAMPLES 7 to 9:

TABLE 3

Rinse aids containing fatty acid N-methyl glucamides and
fatty alcohol EO/PO adducts
Percentages as % by weight
ad 100% by weight water

| Ex. | Glu | c(Glu) % | c(C2) % | CA % | FR % | St. °C. | App. | F |
|---|---|---|---|---|---|---|---|---|
| 7 | A1 | 9.0 | 6.0 | 3.0 | 0.5 | 65 | Clear | 0 |
| 8 | A2 | 9.0 | 6.0 | 3.0 | 0.5 | 65 | Clear | 0 |
| 9 | A3 | 9.0 | 6.0 | 3.0 | 0.5 | 65 | Clear | 0 |

EXAMPLES 10 to 12:

TABLE 4

Rinse aids containing fatty acid N-methyl glucamides and
mixed ethers
Percentages as % by weight
ad 100% by weight water

| Ex. | Glu | c(Glu) % | c(C3) % | CA % | FR % | St. °C. | App. | F |
|---|---|---|---|---|---|---|---|---|
| 10 | A1 | 9.0 | 6.0 | 3.0 | 0.5 | 65 | Clear | 0 |
| 11 | A2 | 9.0 | 6.0 | 3.0 | 0.5 | 65 | Clear | 0 |
| 12 | A3 | 9.0 | 6.0 | 3.0 | 0.5 | 65 | Clear | 0 |

EXAMPLES 13 to 16:

TABLE 5

Rinse aids containing fatty acid N-methyl glucamides,
alkyl oligoglucosides and fatty alcohol polyethylene
glycol ethers
Percentages as % by weight
ad 100% by weight water

| Ex. | c(A1) | c(B1) % | c(C1) % | CA % | FR % | St. °C. | App. | F |
|---|---|---|---|---|---|---|---|---|
| 13 | 7.5 | 10.7 | 0 | 3.0 | 0.5 | >70 | Clear | 0 |
| 14 | 6.0 | 8.6 | 3.0 | 3.0 | 0.5 | >70 | Clear | 1 |
| 15 | 4.5 | 6.4 | 3.0 | 3.0 | 0.5 | >70 | Clear | 0 |
| 16 | 4.0 | 4.3 | 3.0 | 3.0 | 0.5 | 60 | Clear | 1 |

TABLE 6

Drying of the crockery-cutlery articles/clear-rinse effect

| Formulation acc. to Ex. | Glasses | | Knives | | China | | Plastic | |
|---|---|---|---|---|---|---|---|---|
| | D | CRE | D | CRE | D | CRE | D | CRE |
| 1 | 2.5 | 6.2 | 4.2 | 2.1 | 5.0 | 6.4 | 4.0 | 5.3 |
| 3 | 2.9 | 6.0 | 4.2 | 3.1 | 5.0 | 6.7 | 4.2 | 5.6 |
| 4 | 4.4 | 5.8 | 5.0 | 4.6 | 5.0 | 7.3 | 5.0 | 6.7 |
| 5 | 4.6 | 6.2 | 4.7 | 4.9 | 5.0 | 6.7 | 5.0 | 6.2 |
| 6 | 4.2 | 6.0 | 4.9 | 4.4 | 5.0 | 6.7 | 5.0 | 6.5 |
| 7 | 4.1 | 6.0 | 4.9 | 6.5 | 5.1 | 7.7 | 5.0 | 6.8 |
| 8 | 4.3 | 6.3 | 5.0 | 6.1 | 5.0 | 8.0 | 5.0 | 7.0 |
| 9 | 4.6 | 5.6 | 4.6 | 4.9 | 5.0 | 7.3 | 5.0 | 6.8 |
| 10 | 4.0 | 6.1 | 4.5 | 6.3 | 5.1 | 8.0 | 5.0 | 7.0 |
| 11 | 4.7 | 6.0 | 4.4 | 6.0 | 5.0 | 8.0 | 5.0 | 7.0 |
| 12 | 4.8 | 5.6 | 4.6 | 5.2 | 5.0 | 7.7 | 5.0 | 7.0 |
| 13 | 2.5 | 6.1 | 4.2 | 4.3 | 5.0 | 7.6 | 3.6 | 5.8 |
| 14 | 4.0 | 5.9 | 4.6 | 4.7 | 5.0 | 7.9 | 4.3 | 5.9 |
| 15 | 4.5 | 6.1 | 4.8 | 5.8 | 5.0 | 7.7 | 5.0 | 6.4 |
| 16 | 4.4 | 5.9 | 5.0 | 6.4 | 5.0 | 8.0 | 5.0 | 7.0 |
| C1* | 4.8 | 6.0 | 4.8 | 6.6 | 5.0 | 8.0 | 5.0 | 6.8 |

Legend:
D = Drying
CRE = Clear rinse effect
C1 = Commercial rinse aid

We claim:

1. A process for rinsing hard surfaces comprising contacting the hard surfaces with a rinse aid composition consisting of from 0.5% to 20% by weight of fatty acid-N-alkyl polyhydroxyalkyl amides corresponding to formula I:

$$R^1-CO-N-Z \quad\quad (I)$$
$$\overset{|}{R^2}$$

wherein $R^1CO$ is an aliphatic acyl radical containing 6 to 22 carbon atoms, $R^2$ is an alkyl or hydroxyalkyl radical containing 1 to 4 carbon atoms, and Z is a linear or branched polyhydroxyalkyl radical containing 3 to 10 carbon atoms and 3to 10 hydroxyl groups up to 20% by weight of a nonionic surfactant, 1% to 50% by weight of a carboxylic acid, and the balance being water, based on the weight of said composition.

2. The process according to claim 1 wherein in formula I, $R^1CO$ is a $C_{6-12}$ acyl radical, $R^2$ is a methyl group, and Z; is a reduced glucose unit.

3. The process according to claim 1 wherein said nonionic surfactant is selected from the group consisting of fatty alcohol polyethylene glycol ethers, ethoxylated and propoxylated fatty alcohol glycol ethers, mixed ethers, alkyl oligoglucosides, and mixtures thereof.

4. A process for making an ecologically and toxicologically safe aqueous rinse aid composition comprising mixing a composition consisting of from 0.5% to 20% by weight of a fatty acid N-alkyl polyhydroxyalkyl amide corresponding to formula I:

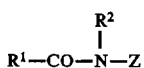
(I)

wherein $R^1CO$ is an aliphatic acyl radical containing 6 to 22 carbon atoms, $R^2$ is an alkyl or hydroxyalkyl radical containing 1 to 4 carbon atoms, and Z is a linear or branched polyhydroxyalkyl radical containing 3 to 10 carbon atoms and 3 to 10 hydroxyl groups, with from 1% to 50% by weight of a carboxylic acid, up to 20% by weight of a nonionic surfactant, the balance being water, based on the weight of said composition.

5. The process according to claim 4 wherein in formula I, $R^1CO$ is a $C_{6-12}$ acyl radical, $R^2$ is a methyl group, and Z is a reduced glucose unit.

6. The process according to claim 4 wherein said nonionic surfactant is selected from the group consisting of fatty alcohol polyethylene glycol ethers, ethoxylated and propoxylated fatty alcohol glycol ethers, mixed ethers, alkyl oligoglucosides, and mixtures thereof.

7. The process according to claim 4 wherein said carboxylic acid is selected from the group consisting of monobasic carboxylic acids, polybasic carboxylic acids, saturated aliphatic dicarboxylic acids, and mixtures thereof.

8. The product of the process of claim 4.
9. The product of the process of claim 5.
10. The product of the process of claim 5.
11. The product of the process of claim 16.
12. The product of the process of claim 7.

13. A process for rinsing hard surfaces comprising contacting the hard surfaces with a rinse aid composition consisting of 1% to 10% by weight of fatty acid N-alkyl glucamides, 3% to 10% by weight of alkyl oligoglucosides, 3% to 10% by weight of fatty alcohol polyglycol ethers, 1% to 30% by weight of citric acid, and the balance, water, based on the weight of said composition.

* * * * *